United States Patent [19]

Kai

[11] Patent Number: 5,820,665
[45] Date of Patent: Oct. 13, 1998

[54] FLUOROALKYLCARBOXYLIC ACID AND DERIVATIVE THEREOF

[75] Inventor: Yoshiaki Kai, Neyagawa, Japan

[73] Assignee: Matsushita Electric Industrial Co., Ltd., Japan

[21] Appl. No.: 864,427

[22] Filed: May 28, 1997

Related U.S. Application Data

[62] Division of Ser. No. 601,360, Feb. 16, 1996, Pat. No. 5,669,964.

[30] Foreign Application Priority Data

Feb. 16, 1995 [JP] Japan ................................. 7-028486
Jul. 24, 1995 [JP] Japan ................................. 7-186798

[51] Int. Cl.$^6$ ............... C07C 323/23; C07C 323/25; C07C 323/27; C07C 323/03; C07C 323/05; C07C 323/12; C07C 323/14

[52] U.S. Cl. ............... 106/287.28; 106/287.24; 106/287.25; 106/287.26; 106/2; 562/840; 564/204; 564/209; 564/500; 568/56

[58] Field of Search ............. 106/287.24, 287.25, 106/287.26, 287.28, 2; 562/840; 568/204, 209, 500, 56

[56] References Cited

U.S. PATENT DOCUMENTS 4,239,915 12/1980 Falk ........................... 562/481
4,855,025 8/1989 Gautier et al. ............. 204/157.86

FOREIGN PATENT DOCUMENTS 62-29427 6/1987 Japan.
2-59131 12/1990 Japan.

OTHER PUBLICATIONS

Kai, *Chem. Abstr.*, 126:56974 (1996) Oct.

Primary Examiner—David Brunsman
Attorney, Agent, or Firm—Wenderoth, Lind & Ponack

[57] ABSTRACT

An object of the present invention is to provide a compound which imparts a sufficient water repellency and a suitable oil repellency to substrates such as a fiber, a paper, a wood material, a hide, a leather, a resin, a glass, a metal, etc. The compound of the present invention is a fluoroalkylcarboxylic acid of the general formula (I), and its derivative of the general formula (II) (e.g. fluoroalkyl alcohol, fluoroalkyl carboxylic acid chloride, fluoroalkylcarboxylic acid amide and fluoroalkylamine).

$$R_1-R_2-(S)_q \diagdown CH(CH_2)_t COOH \quad (I)$$
$$Rf(CH_2)_p(S)_r \diagup$$

$$R_1-R_2-(S)_q \diagdown CH(CH_2)_t-Z \quad (II)$$
$$Rf(CH_2)_p(S)_r \diagup$$

4 Claims, 4 Drawing Sheets

FLUOROALKYLCARBOXYLIC ACID AND DERIVATIVE THEREOF

This is a divisional application of Ser. No. 08/601,360, filed Feb. 16, 1996 now U.S. Pat. No. 5,669,969.

FIELD OF THE INVENTION

The present invention relates to a novel fluoroalkylcarboxylic acid and a derivative thereof, which are useful as a raw material and an intermediate of the fluorochemical industry, and a water repellent which imparts a water repellency and an oil repellency to substrates such as a fiber, a paper, a wood material, a hide, a leather, a resin, a glass, a metal, etc.

RELATED ARTS

As an organic compound having two perfluoroalkyl groups in the same molecule, for example, a perfluoroalkylcarboxylic acid of the following formula (i) has hitherto been suggested (Japanese Patent Publication No. 62-29427).

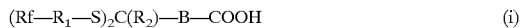
$$(Rf-R_1-S)_2C(R_2)-B-COOH \qquad (i)$$

wherein Rf is a linear or branched perfluoroalkyl group having 6 to 12 carbon atoms; $R_1$ is a linear or branched alkylene group having 2 to 4 carbon atoms; $R_2$ is an alkyl group having 1 or 2 carbon atoms or —B—COOH; and B is a covalent bond or an alkylene group having 1 to 3 carbon atoms.

In addition, as a conventional example of an organic compound having molecular chains and a polar group in the same molecule, wherein one molecular chain is a perfluoroalkyl group and another molecular chain is an aliphatic alkyl group, and these groups bond each other through a carbon-carbon covalent bond, for example, a mixture of perfluoro compounds of the formulas (A) and (B) (the molar ratio of the compound (A) to the compound (B) is 0.1 to 10) has been proposed (Japanese Patent Publication No. 2-59131).

wherein $R_F$ is a linear or branched perfluoroalkyl group having 4 to 12 carbon atoms; m is an integer of 1 or 2; n is an integer of 4 to 11; X is an OH group or a $NR_1R_2$ group, provided that $R_1$ and $R_2$ may be the same or different and each is a hydrogen atom or a methyl group.

However, the perfluoroalkylcarboxylic acid of the above formula (i) has two sulfur atoms connected to a water repellent group (Rf—$R_1$). Therefore, there was a problem that a sufficient water repellency can not be imparted to the substrate when using the perfluorocarboxylic acid (i) as the water repellent. Regarding the mixture of perfluorocompounds of the above formulas (A) and (B), one molecular chain is limited to a lipophilic aliphatic alkyl group. Therefore, there was a problem that the wide oil repellency can not be imparted to the substrate when using the mixture as the water repellent.

SUMMARY OF THE INVENTION

The compound of the present invention solves the above conventional problems, and an object of the present invention is to provide a novel fluoroalkylcarboxylic acid and derivative thereof which have molecular chains and a polar group in the same molecule, wherein one molecular chain is a fluoroalkyl group or a fluoroalkenyl group and another molecular chain is an aliphatic hydrocarbon group, a fluoroalkyl group or a fluoroalkenyl group, and wherein only one molecular chain contains a sulfur atom or contains no sulfur atom and the number of carbon atoms of an alkylene group which bonds with each group can be widely changed, and is to provide a water repellent which imparts a sufficient water repellency and a suitable oil repellency to substrates such as a fiber, a paper, a wood material, a hide, a leather, a resin, a glass, a metal, etc.

The compound for achieving the above object of the present invention is a fluoroalkylcarboxylic acid of the formula (I), and its derivative of the formula (II) (e.g. fluoroalkyl alcohol, fluoroalkylcarboxylic acid chloride, fluoroalkylcarboxylic acid amide and fluoroalkylamine).

wherein $R_1$ is a fluoroalkyl, fluoroalkenyl or aliphatic hydrocarbon group having 1 to 20 carbon atoms; $R_2$ is an alkylene or alkenylene group having 1 to 11 carbon atoms; Rf is a fluoroalkyl or fluoroalkenyl group having 1 to 20 carbon atoms; p is an integer of 1 to 11; q+r is 0 or 1; and t is 0 or an integer of 1 to 8; provided that p is an integer of 3 to 11 when $R_1$ is an aliphatic hydrocarbon group, $R_2$ is an alkylene group, q+r is 0 and t is 0.

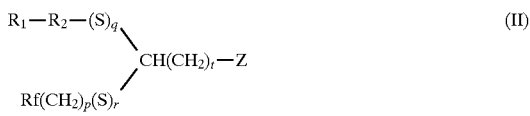

wherein $R_1$ is a fluoroalkyl, fluoroalkenyl or aliphatic hydrocarbon group having 1 to 20 carbon atoms; $R_2$ is an alkylene or alkenylene group having 1 to 11 carbon atoms; Rf is a fluoroalkyl or fluoroalkenyl group having 1 to 20 carbon atoms; Z is $CH_2OH$, $COCl$, $CONH_2$ or $CH_2NH_2$; p is an integer of 1 to 11; q+r is 0 or 1; and t is 0 or an integer of 1 to 8; provided that p is an integer of 3 to 11 when $R_1$ is an aliphatic hydrocarbon group, $R_2$ is an alkylene group, q+r is 0 and t is 0.

DETAILED DESCRIPTION OF THE INVENTION

Figure 1:
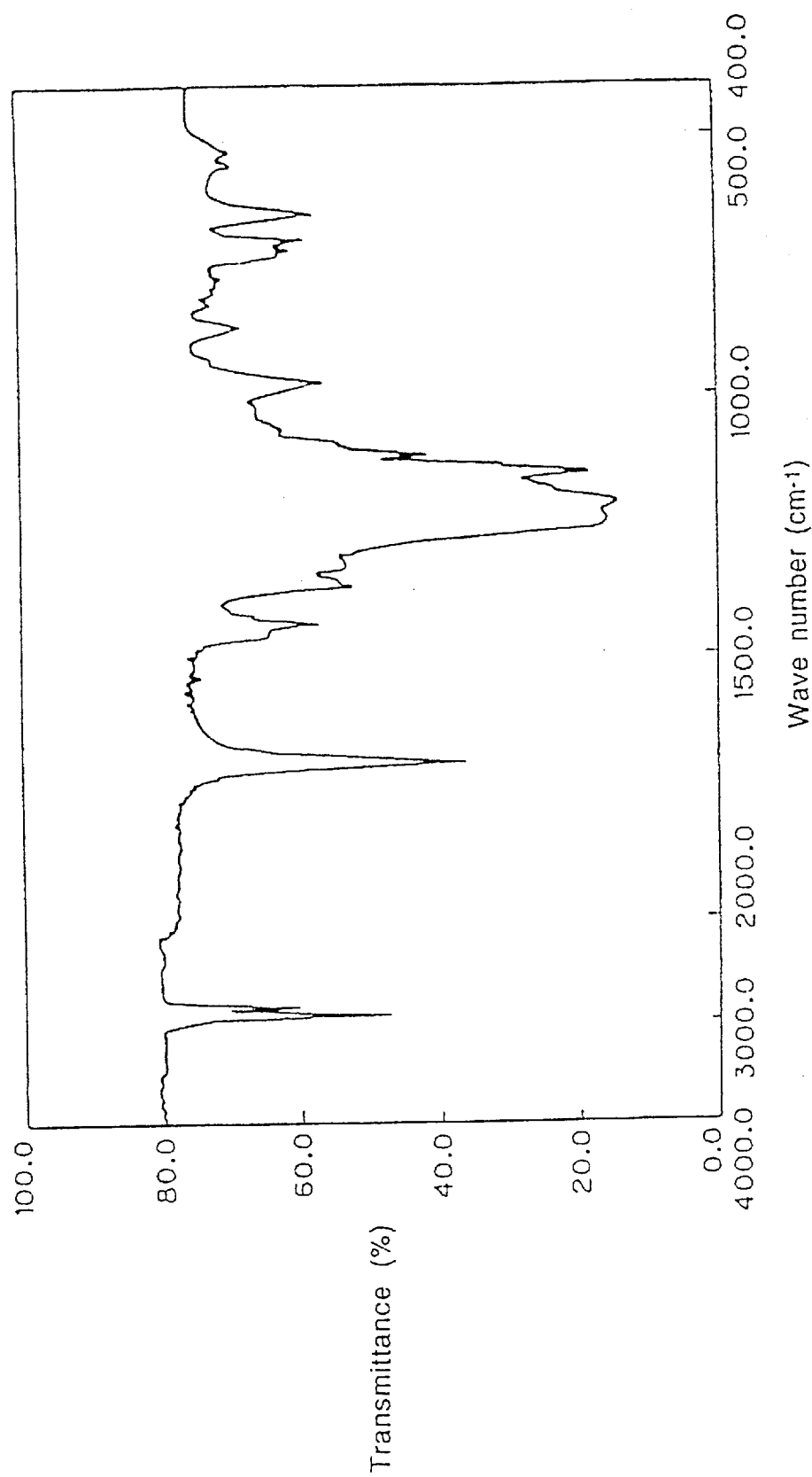
FIG. 1 shows an IR spectrum chart of the product obtained in Example 1.

In view of easy handling (e.g. solubility in a solvent, etc.), it is preferred that $R_1$ is a fluoroalkyl, fluoroalkenyl or aliphatic hydrocarbon group having 1 to 20 carbon atoms; Rf is a fluoroalkyl or fluoroalkenyl group having 1 to 20 carbon atoms. It is preferable that p and q each is an integer of 1 to 11; and u is 0 or an integer of 1 to 8. A preferred range with respect to p, q and u is based on economy of a raw material, and it is also possible to produce by using those having carbon atoms more than this range.

The production process of a fluoroalkylcarboxylic acid of the formula (III) included in the compound of the present invention can be conducted by reacting a monohalo-substituted fluoroalkylcarboxylate ester of the formula (IV) with a thiol of the formula (V) in the presence of a catalyst of a base to synthesize a fluoroalkylcarboxylate ester of the formula (VI), followed by the ester hydrolysis of this fluoroalkylcarboxylate ester according to a conventional method.

(III)

wherein $R_1$ is a fluoroalkyl, fluoroalkenyl or aliphatic hydrocarbon group having 1 to 20 carbon atoms; $R_2$ is an alkylene or alkenylene group having 1 to 11 carbon atoms; Rf is a fluoroalkyl or fluoroalkenyl group having 1 to 20 carbon atoms; and t is 0 or an integer of 1 to 8.

$$RfCH_2CHX(CH_2)_tCOOR_3 \quad (IV)$$

wherein Rf is a fluoroalkyl or fluoroalkenyl group having 1 to 20 carbon atoms; $R_3$ is an aliphatic hydrocarbon group, X is Br or I; and t is 0 or an integer of 1 to 3.

(V)

wherein $R_1$ is a fluoroalkyl, fluoroalkenyl or aliphatic hydrocarbon group having 1 to 20 carbon atoms; and $R_2$ is an alkylene or alkenylene group having 1 to 11 carbon atoms.

(VI)

wherein $R_1$ is a fluoroalkyl, fluoroalkenyl or aliphatic hydrocarbon group having 1 to 20 carbon atoms; $R_2$ is an alkylene or alkenylene group having 1 to 11 carbon atoms; $R_3$ is an aliphatic hydrocarbon group; Rf is a fluoroalkyl or fluoroalkenyl group having 1 to 20 carbon atoms; and t is 0 or an integer of 1 to 8.

The production process of a fluoroalkylcarboxylic acid of the formula (VII) included in the compound of the present invention can be conducted by reacting an α-halo-fluoroalkylcarboxylic acid of the formula (VIII) with the thiol of the formula (V) in the presence of a catalyst of a base.

(VII)

wherein $R_1$ is a fluoroalkyl, fluoroalkenyl or aliphatic hydrocarbon group having 1 to 20 carbon atoms; $R_2$ is an alkylene or alkenylene group having 1 to 11 carbon atoms; Rf is a fluoroalkyl or fluoroalkenyl group having 1 to 20 carbon atoms; and p is an integer of 1 to 11.

$$Rf(CH_2)_pCHXCOOH \quad (VIII)$$

wherein Rf is a fluoroalkyl or fluoroalkenyl group having 1 to 20 carbon atoms; X is Cl, Br or I; and p is an integer of 1 to 11.

The production process of a fluoroalkylcarboxylic acid of the formula (IX) included in the compound of the present invention can be conducted by reacting an α-halo-alkylcarboxylic acid of the formula (X) with a thiol of the formula (XI) in the presence of a catalyst of a base.

(IX)

wherein $R_1$ is a fluoroalkyl, fluoroalkenyl or aliphatic hydrocarbon group having 1 to 20 carbon atoms; $R_2$ is an alkylene or alkenylene group having 1 to 11 carbon atoms; Rf is a fluoroalkyl or fluoroalkenyl group having 1 to 20 carbon atoms; and p is an integer of 1 to 11.

$$R_1{-}R_2{-}CHXCOOH \quad (X)$$

wherein $R_1$ is a fluoroalkyl, fluoroalkenyl or aliphatic hydrocarbon group having 1 to 20 carbon atoms; $R_2$ is an alkylene or alkenylene group having 1 to 11 carbon atoms; and X is Cl, Br or I.

$$Rf(CH_2)_pSH \quad (XI)$$

wherein Rf is a fluoroalkyl or fluoroalkenyl group having 1 to 20 carbon atoms; and p is an integer of 1 to 11.

As the basic catalyst in the production of the fluoroalkylcarboxylic acids of the formulas (III), (VII) and (IX), it is possible to use alkaline metal carbonate salts (e.g. $NaCO_3$, $KCO_3$, etc.), alkaline earth metal carbonate salts (e.g. $Ca(CO_3)_2$, $Mg(CO_3)_2$, etc.) and alkoxides of alkaline metals. As the solvent, it is suitable to use ketones (e.g. acetone, methyl ethyl ketone, methyl isobutyl ketone, etc.) and ethers (e.g. tetrahydrofuran, dioxane, etc.).

The production process of a fluoroalkylcarboxylic acid of the formula (XII) included in the compound of the present invention can be conducted by reacting a monohalo-substituted fluoroalkylcarboxylate ester of the formula (XIII) with an α-olefin of the formula (XIV) in the presence of a radical initiator as the catalyst to synthesize a fluoroalkylcarboxylate ester of the formula (XV), followed by dehalohydrogenation and ester hydrolysis of this fluoroalkylcarboxylate ester in the presence of a basic catalyst.

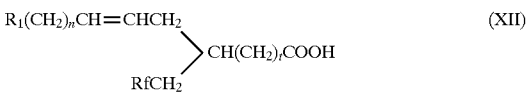
(XII)

wherein $R_1$ is a fluoroalkyl, fluoroalkenyl or aliphatic hydrocarbon group having 1 to 20 carbon atoms; Rf is a fluoroalkyl or fluoroalkenyl group having 1 to 20 carbon atoms; n is an integer of 1 to 8; and t is 0 or an integer of 1 to 8.

$$RfCH_2CHX(CH_2)_tCOOR_3 \quad (XIII)$$

wherein Rf is a fluoroalkyl or fluoroalkenyl group having 1 to 20 carbon atoms; $R_3$ is an aliphatic hydrocarbon group; X is Br or I; and t is 0 or an integer of 1 to 8.

$$R_1(CH_2)_{n+1}CH{=}CH_2 \quad (XIV)$$

wherein $R_1$ is a fluoroalkyl, fluoroalkenyl or aliphatic hydrocarbon group having 1 to 20 carbon atoms; and n is an integer of 1 to 8.

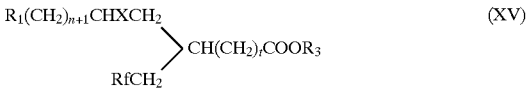
(XV)

wherein $R_1$ is a fluoroalkyl, fluoroalkenyl or aliphatic hydrocarbon group having 1 to 20 carbon atoms; Rf is a fluoroalkyl or fluoroalkenyl group having 1 to 20 carbon atoms; $R_3$ is an aliphatic hydrocarbon group; X is Br or l; n is an integer of 1 to 8; and t is 0 or an integer of 1 to 8.

The production process of a fluoroalkylcarboxylic acid of the formula (XVI) included in the compound of the present invention can be conducted by reacting an α-halo-fluoroalkylcarboxylate ester of the formula (XVII) with the α-olefin of the formula (XIV) in the presence of a radical initiator as the catalyst to synthesize a fluoroalkylcarboxylate ester of the formula (XVIII), followed by dehalohydrogenation and ester hydrolysis of this fluoroalkylcarboxylate ester in the presence of a basic catalyst.

(XVI)

wherein $R_1$ is a fluoroalkyl, fluoroalkenyl or aliphatic hydrocarbon group having 1 to 20 carbon atoms; Rf is a fluoroalkyl or fluoroalkenyl group having 1 to 20 carbon atoms; n is an integer of 1 to 8; and p is an integer of 1 to 11.

(XVII)

wherein Rf is a fluoroalkyl or fluoroalkenyl group having 1 to 20 carbon atoms; $R_3$ is an aliphatic hydrocarbon group; X is Br or l; and p is an integer of 1 to 11.

(XVIII)

wherein $R_1$ is a fluoroalkyl, fluoroalkenyl or aliphatic hydrocarbon group having 1 to 20 carbon atoms; Rf is a fluoroalkyl or fluoroalkenyl group having 1 to 20 carbon atoms; $R_3$ is an aliphatic hydrocarbon group; X is Br or l; n is an integer of 1 to 8; and P is an integer of 1 to 11.

As the radical initiator in the synthesis of the fluoroalkylcarboxylate esters of the formulas (XV) and (XVIII), it is possible to use potassium persulfate, ammonium persulfate, t-butyl hydroperoxide, di-t-butyl peroxide, cumene hydroperoxide, acetyl peroxide, benzoyl peroxide, lauroyl peroxide, azobisisobutyronitrile, azobis-2,4-dimethylvaleronitrile, azobiscyclohexanecarbonitrile, methyl azobisisobutyrate, azobisisobutylamidine hydrochloride, azobiscyanovaleric acid, etc. In addition, as the solvent in the synthesis thereof, it is possible to use paraffin hydrocarbons, aromatic hydrocarbons, halogenated hydrocarbon, etc. No solvent may be used.

The production process of a fluoroalkylcarboxylic acid of the formula (XIX) included in the compound of the present invention can be conducted by reducing the fluoroalkylcarboxylate ester of the formula (XV) with a metal hydride to synthesize a fluoroalkylcarboxylate ester of the formula (XX), followed by the ester hydrolysis of this fluoroalkylcarboxylate ester in the presence of a basic catalyst.

(XIX)

wherein $R_1$ is a fluoroalkyl, fluoroalkenyl or aliphatic hydrocarbon group having 1 to 20 carbon atoms; Rf is a fluoroalkyl or fluoroalkenyl group having 1 to 20 carbon atoms; n is an integer of 1 to 8; and t' is an integer of 1 to 8.

(XX)

wherein $R_1$ is a fluoroalkyl, fluoroalkenyl or aliphatic hydrocarbon group having 1 to 20 carbon atoms; Rf is a fluoroalkyl or fluoroalkenyl group having 1 to 20 carbon atoms; $R_3$ is an aliphatic hydrocarbon group; n is an integer of 1 to 8; and t' is an integer of 1 to 8.

The production process of a fluoroalkylcarboxylic acid of the formula (XXI) included in the compound of the present invention can be conducted by reducing the fluoroalkylcarboxylate ester of the formula (XVIII) with a metal hydride to synthesize a fluoroalkylcarboxylate ester of the formula (XXII), followed by the ester hydrolysis of this fluoroalkylcarboxylate ester in the presence of a basic catalyst.

(XXI)

wherein $R_1$ is a fluoroalkyl, fluoroalkenyl or aliphatic hydrocarbon group having 1 to 20 carbon atoms; Rf is a fluoroalkyl or fluoroalkenyl group having 1 to 20 carbon atoms; n is an integer of 1 to 8; and p is an integer of 1 to 11; provided that p is an integer of 3 to 11 when $R_1$ is an aliphatic hydrocarbon group.

(XXII)

wherein $R_1$ is a fluoroalkyl, fluoroalkenyl or aliphatic hydrocarbon group having 1 to 20 carbon atoms; Rf is a fluoroalkyl or fluoroalkenyl group having 1 to 20 carbon atoms; $R_3$ is an aliphatic hydrocarbon group; n is an integer of 1 to 8; and p is an integer of 1 to 11; provided that p is an integer of 3 to 11 when $R_1$ is an aliphatic hydrocarbon group.

As the metal hydride used in the synthesis of the fluoroalkylcarboxylate esters of the formulas (XX) and (XXII), it is possible to use $NaBH_4$, $NaBH_3CN$, $LiBH(C_2H_5)_3$, etc. As the solvent thereof, it is possible to use anhydrous tetrahydrofuran (anhydrous THF), anhydrous alcohol, anhydrous halogenated hydrocarbon, anhydrous aromatic hydrocarbon, etc.

As the basic catalysts used in the production of the fluoroalkylcarboxylic acids of the formulas (XII), (XVI), (XIX) and (XXI), it is possible to use alkaline hydroxides (e.g. NaOH, KOH, etc.), alkaline earth hydroxides (e.g. $Ca(OH)_2$, $Mg(OH)_2$, etc.), alkaline carbonate salts (e.g. $NaCO_3$, $KCO_3$, etc.) and alkaline earth carbonate salts (e.g. $Ca(CO_3)_2$, $Mg(CO_3)_2$, etc.). As the solvent thereof, alcohols containing 1 to 50 volume % of water are suitable.

In addition, the production process of the fluoroalkylcarboxylic acid of the formula (XIX) can also be conducted by hydrogenating the fluoroalkylcarboxylic acid of the formula (XII) in the presence of a metal or metal oxide catalyst.

Similarly, the production process of the fluoroalkylcarboxylic acid of the formula (XXI) can also be conducted by hydrogenating the fluoroalkylcarboxylic acid of the formula (XVI) in the presence of the metal or metal oxide catalyst.

As the metal or metal oxide catalyst in this case, it is possible to use Raney-nickel, palladium black, platinum black, palladium oxide, platinum oxide, etc. As the solvent thereof, ethers and alcohols are suitable.

Further, the derivatives of the fluoroalkylcarboxylic acid of the present invention (i.e. fluoroalkyl alcohol, fluoroalkyl carboxylic acid chloride, fluoroalkylcarboxylic acid amide and fluoroalkylamine) represented by the formula (II) can be easily produced by a conventional known method, respectively. (cf. Japanese Laid-Open Patent Publication Nos. 2-288841, 5-331475 and 6-293703).

The fluoroalkylcarboxylic acid and its derivative thereof according to the present invention have molecular chains and a polar group in the same molecule, wherein one molecular chain is a fluoroalkyl group or a fluoroalkenyl group and another molecular chain is an aliphatic hydrocarbon group, a fluoroalkyl group or a fluoroalkenyl group, and wherein only one molecular chain contains a sulfur atom or contains no sulfur atom and the number of carbon atoms of an alkylene group which bonds with each group can be widely changed.

A sulfur atom in the molecular chain has a hydrogen bonding force which is smaller than that of a nitrogen or oxygen atom but is larger than a carbon-carbon covalent bond and, therefore, the sulfur atom in the molecular chain acts as a hydrophilic group. Therefore, it is preferred that the number of sulfur atoms in the molecule of the water repellent is as small as possible.

By the way, the alkylene group which bonds to the aliphatic hydrocarbon group and above each group has a lipophilic property and, therefore, the oil repellency can be widely modified by changing the aliphatic hydrocarbon group to a fluorine chain or changing the chain length of the alkylene group.

Accordingly, the water repellent of the present invention can impart a sufficient water repellency to substrates such as a fiber, a paper, a wood material, a hide, a leather, a resin, a glass, a metal, etc. and impart an oil repellency or a lipophilic property widely modified according to the application. Therefore, a sufficient water repellency and a suitable oil repellency can be imparted to these substrates without inhibiting adhesive properties.

DESCRIPTION OF PREFERRED EMBODIMENTS

The present invention will be illustrated hereinafter with reference to the following examples which do not limit the present invention.

EXAMPLE 1

Hereinafter, the first embodiment of the present invention will be explained in detail.

The compound of this embodiment is represented by the formula (1).

(1)

Comparing the compound of the formula (1) with that of the general formula (I), it is one wherein $R_1$ is a fluoroalkyl group having 8 carbon atoms, Rf is a fluoroalkyl group having 8 carbon atoms, $R_2$ is an alkylene group having 2 carbon atoms, p is 1, q is 1, r is 0 and t is 8.

Next, the production process of the compound of the formula (1) will be explained.

As the starting material, a monohalo-substituted fluoroalkylcarboxylate ester of the formula (2) and a known perfluorooctylethanethiol of the formula (3) are used. This monohalo-substituted fluoroalkylcarboxylate ester is synthesized from a perfluoroalkyliodide and a ω-alkenylcarboxylate ester (Japanese Laid-Open Patent Publication No. 2-288841).

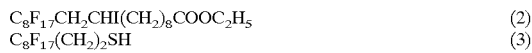

The monohalo-substituted fluoroalkylcarboxylate ester of the formula (2) (74.4 g, 0.10 mol), perfluorooctylethanethiol (48.0 g, 0.10 mol), potassium carbonate (13.8 g, 0.10 mol) and methyl isobutyl ketone (MIBK, 300 ml) were charged in a 1 liter flask equipped with a stirring blade, and the mixture was reacted under reflux with stirring continuously for 48 hours. After the completion of the reaction, MIBK was distilled off under a reduced pressure. 500 ml of a 90 volume % ethanol solution (containing 10 volume % of the distilled water) containing sodium hydroxide (44 g) was added to the resulting fluoroalkylcarboxylate intermediate, and followed by reflux for 4 hours. After cooling the solution, 300 ml of 4N hydrochloric acid was slowly added with stirring and the solution was further stirred at 70° C. for 2 hours. Then, the reaction product was filtered under a reduced pressure and dissolved in 500 ml of ethyl acetate. The solution was repeatedly washed with the distilled water until the pH became 7, and dried over anhydrous sodium sulfate. Then, ethyl acetate was distilled off and the reaction product was recrystallized from an ethanol solution at 0° C. to give 92 g of a white solid having a melting point of 52° C. This white solid was subjected to an infrared spectroscopy (IR), a gel permeation chromatography (GPC) and an organic mass spectrometry (FD-MS). As a result, it has been found that the white solid is a fluoroalkylcarboxylic acid of the formula (1), which contains no starting material, intermediate and by-product.

IR: Absorption peak at 1700 cm$^{-1}$ of carboxylic acid was shown (FIG. 1).

GPC: No starting material, intermediate and by-product were detected.

FD-MS: Main peak was shown at m/e 1083.

Further, in this embodiment, the production process of the compound of the formula (I) wherein $R_1$ is a fluoroalkyl group having 8 carbon atoms and $R_2$ is an alkylene group having 2 carbon atoms was explained. In case that the chain length is different from the above, the compound of the formula (5) can also be produced by using the compound of the formula (4) as the starting material in place of perfluorooctylethanethiol. In addition, in case that $R_1$ is an aliphatic hydrocarbon group or $R_1$ is a fluoroalkenyl group and $R_2$ is an alkenylene group, the compound of the formula (7) or (8) can also be produced by using decanethiol or the compound of the formula (6) as the starting material in place of perffluorooctylethanethiol.

$C_4F_9(CH_2)_{11}SH$ (4)

$C_6F_{11}CH=CH(CH_2)_2SH$ (6)

-continued $$C_6F_{11}CH=CH(CH_2)_2S \diagdown CH(CH_2)_8COOH \atop C_8F_{17}CH_2 \diagup \qquad (8)$$

Furthermore, in this embodiment, the production process of the compound of the formula (I) wherein t is 8 was explained. In case that t indicates the other numeral, the compound of the formula (10) can also be produced by using a monohalo-substituted fluoroalkylcarboxylate of the formula (9) as the starting material in place of that of the formula (2).

$$C_8F_{17}CH_2CHICH_2COOC_2H_5 \qquad (9)$$

$$C_8F_{17}(CH_2)_2S \diagdown CHCH_2COOH \atop C_8F_{17}CH_2 \diagup \qquad (10)$$

EXAMPLE 2

Hereinafter, the second embodiment of the present invention will be explained in detail.

The compound of this embodiment is represented by the formula (11).

$$C_{16}H_{33} \diagdown CHCOOH \atop C_8F_{17}(CH_2)_2S \diagup \qquad (11)$$

Comparing the compound of the formula (11) with that of the general formula (i), it is one wherein the $R_1$-containing molecular chain ($R_1$—$R_2$—) is an aliphatic hydrocarbon group having 16 carbon atoms, Rf is a fluoroalkyl group having 8 carbon atoms, p is 2, q is 0, r is 1 and t is 0.

Next, the production process of the compound of the formula (11) will be explained.

α-Bromostearic acid (36.3 g, 0.10 mol), perfluorooctylethanethiol (48.0 g, 0.10 mol), potassium carbonate (13.8 g, 0.10 mol) and MIBK (300 ml) were charged in a 1 liter flask equipped with a stirring blade, and the mixture was reacted under reflux with stirring continuously for 48 hours. After the completion of the reaction, the solution was cooled and 30 ml of 4N hydrochloric acid was slowly added with stirring. After dissolving in 500 ml of ethyl acetate, the solution was repeatedly washed with the distilled water until the pH became 7, and dried over anhydrous sodium sulfate. Then, the solvent was distilled off and the reaction product was recrystallized from an ethanol solution at 0° C. to give 95 g of a white solid having a melting point of 66° C. This white solid was subjected to IR, GPC and FD-MS. As a result, it has been found that the white solid is a fluoroalkylcarboxylic acid of the formula (11), which contains no starting material and by-product.

Figure 2:
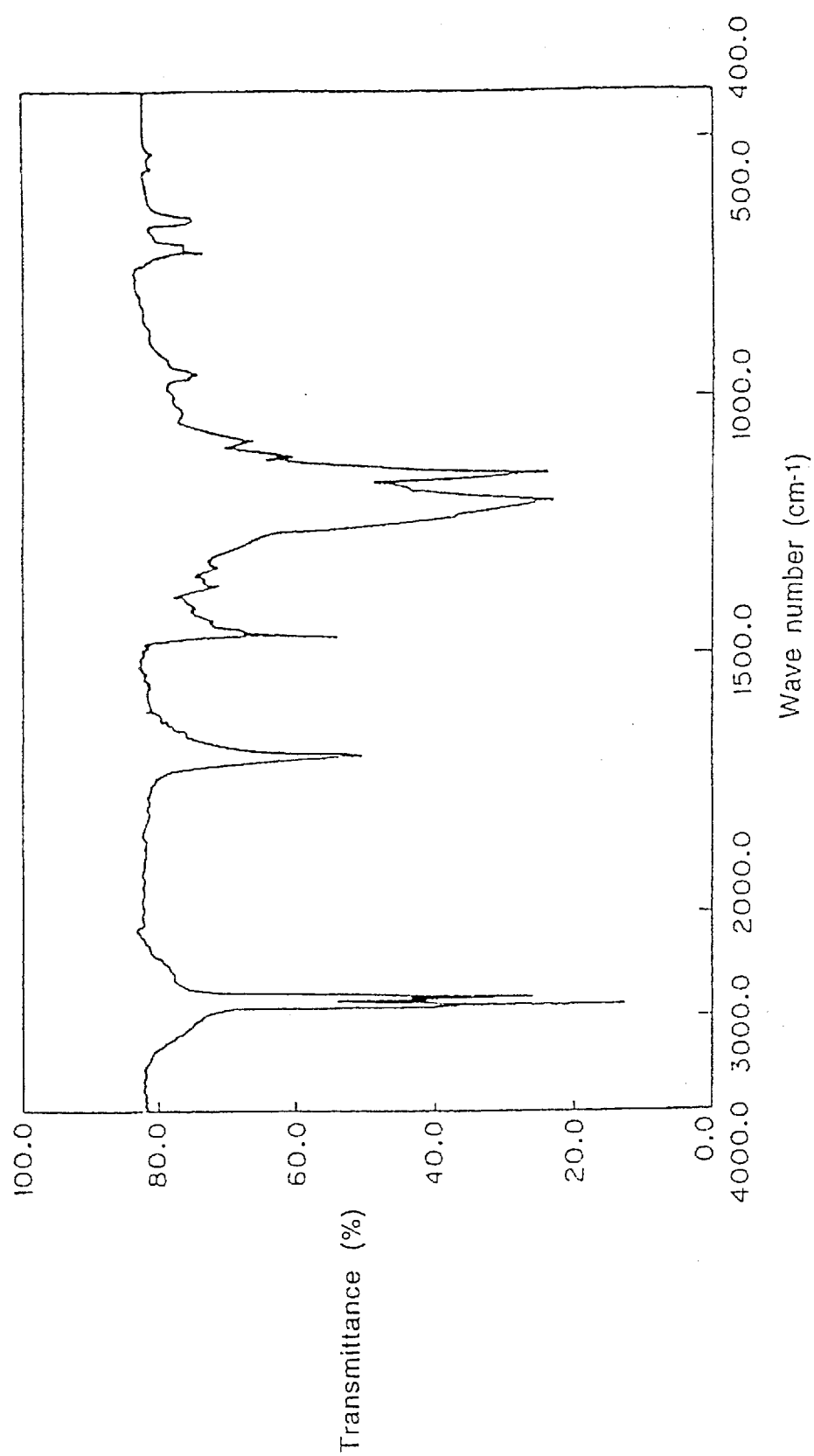
FIG. 2 shows an IR spectrum chart of the product obtained in Example 2.

IR: Absorption peak at 1700 cm$^{-1}$ of carboxylic acid was shown (FIG. 2)

GPC: No starting material and by-product were detected.

FD-MS: Main peak was shown at m/e 763.

Further, in this embodiment, the production process of the compound of the formula (I) wherein the $R_1$-containing molecular chain is an aliphatic hydrocarbon group having 16 carbon atoms was explained. In case of the aliphatic hydrocarbon group having different chain length, the compound can also be produced by using an α-bromoaliphatic alkylcarboxylic acid having different chain length as the starting material in place of α-bromostearic acid. In addition, in case that $R_1$ is a fluoroalkyl group or a fluoroalkenyl group, the compound of the formula (14) or (15) can also be produced by using the compound of the formula (12) or (13) as the starting material in place of α-bromostearic acid.

$$C_8F_{17}(CH_2)_9CHBrCOOH \qquad (12)$$
$$C_6F_{11}(CH_2)_9CHBrCOOH \qquad (13)$$

$$C_8F_{17}(CH_2)_9 \diagdown CHCOOH \atop C_8F_{17}(CH_2)_2S \diagup \qquad (14)$$

$$C_6F_{11}(CH_2)_9 \diagdown CHCOOH \atop C_8F_{17}(CH_2)_2S \diagup \qquad (15)$$

This α-bromofluoroalkylcarboxylic acid is synthesized from a fluoroalkylcarboxylic acid, red phosphorus and bromine (Japanese Laid-Open Patent Publication No. 5-331475).

Furthermore, in this Example, the production process of the compound of the formula (I) wherein q is 0 and r is 1 was explained. In case that q is 1 and r is 0, the compound of the formula (16) can also be produced by using the compound of the formula (12) as the starting material in place of α-bromostearic acid and using decanethiol in place of perfluorooctylethanethiol.

$$C_{10}H_{21}S \diagdown CHCOOH \atop C_8F_{17}(CH_2)_9 \diagup \qquad (16)$$

EXAMPLE 3

Hereinafter, the third embodiment of the present invention will be explained in detail.

The compound of this embodiment is represented by the formula (17).

$$C_{15}H_{31}CH=CHCH_2 \diagdown CHCOOH \atop C_8F_{17}(CH_2)_9 \diagup \qquad (17)$$

Comparing the compound of the formula (17) with the compound of the general formula (I), it is one wherein $R_1$ is an aliphatic hydrocarbon group having 15 carbon atoms, $R_2$ is an alkenylene group having 3 carbon atoms, Rf is a fluoroalkyl group having 8 carbon atoms, p is 9, q is 0, r is 0 and t is 0.

Next, the production process of the compound of the formula (17) will be explained.

As the starting material, ethyl α-bromofluoroalkylcarboxylate of the formula (18) and 1-octadecene of the formula (19) were used.

$$C_8F_{17}(CH_2)_9CHBrCOOC_2H_5 \qquad (18)$$

$$CH_2=CHC_{16}H_{33} \qquad (19)$$

Next, the production process of the compound of the formula (17) will be explained.

Ethyl α-bromofluoroafkylcarboxylate (391.0 g, 0.57 mol) of the formula (18) as the starting material and n-octane (500 ml) were charged in a 1 liter flask equipped with a stirring blade and, after heating to a reflux temperature (about 130° C.), a mixed solution of 1-octadecene (144.5 g, 0.57 mol) and di-t-butyl peroxide (DTPO, 5.4 g) was added dropwise with stirring over about 3 hours. After further stirring for 3 hours under reflux, 100 ml of n-octane in which DTPO (5.4 g) was dissolved was added dropwise over about 2 hours. Furthermore, the reflux was carried out continuously for 15 hours to complete the reaction. After the completion of the reaction, n-octane was distilled off under a reduced pressure. Then, the reaction product was dissolved in 2 liter of n-hexane and, after cooling to 0° C., the precipitated by-product was removed. Furthermore, n-hexane was distilled off and the reaction product was recrystallized from a methanol solution at 0° C. to give 64 g of a fluoroalkylcarboxylate of the formula (20) as the intermediate.

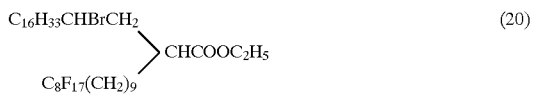
(20)

This fluoroalkylcarboxylate ester (64 g, 0.07 mol) was charged in a 1 liter flask equipped with a stirring blade, and 500 ml of a 90% ethanol solution (containing 10 volume % of the distilled water) in which 44 g of sodium hydroxide was dissolved was added and the mixture was refluxed for 18 hours. After cooling the solution, 300 ml of 4N hydrochloric acid was slowly added with stirring and, further, the solution was stirred at 70° C. for 2 hours. The reaction product was filtered under a reduced pressure and dissolved in 500 ml of ethyl acetate. Then, the solution was repeatedly washed with distilled water until the pH became 7, and dried over anhydrous sodium sulfate. Then, ethyl acetate was distilled off and the reaction product was recrystallized from an ethanol solution at 0° C. to give 55 g of a white solid having a melting point of 66° C. This white solid was subjected to $^{13}C$—NMR, IR, GPC and FD-MS. As a result, it has been found that the white solid is a fluoroalkylcarboxylic acid of the formula (17), which contains no starting material, intermediate and by-product.

$^{13}C$—NMR: Signal of double bond was observed at 125.5 and 128.0 ppm.

Figure 3:
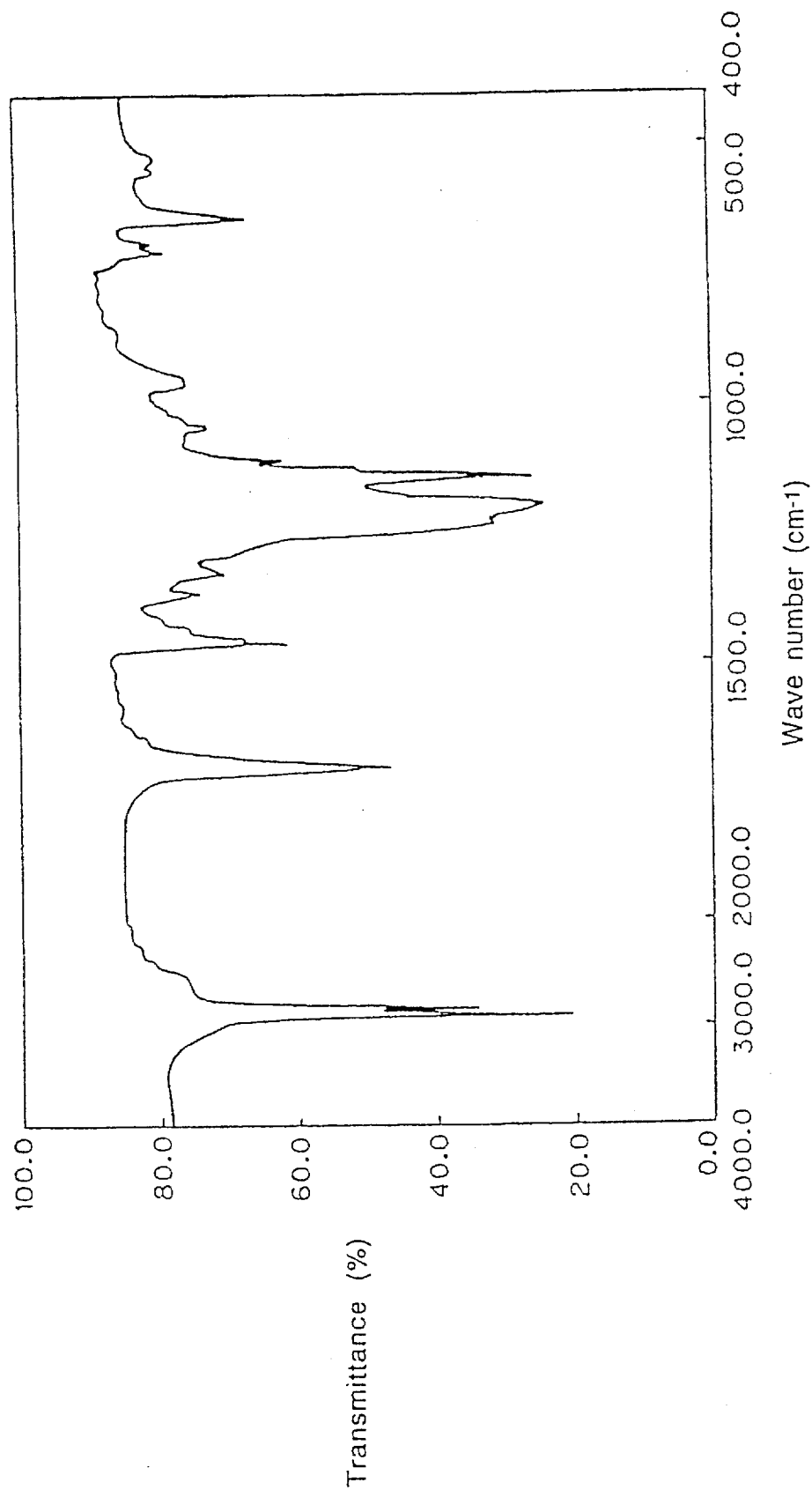
FIG. 3 shows an IR spectrum chart of the product obtained in Example 3.

IR: Absorption peak at 1700 cm$^{-1}$ of carboxylic acid was shown (FIG. 3).

GPC: No starting material, intermediate and by-product were detected.

FD-MS: Main peak was shown at m/e 855.

Further, in this embodiment, the production process of the formula (I) wherein the $R_1$-containing molecular chain is an aliphatic hydrocarbon group having 18 carbon atoms was explained. In case of the aliphatic hydrocarbon group having different chain length, the compound can also be produced by using 1-olefin other than that having 18 carbon atoms as the raw material in place of 1-octadecene. In addition, in case that the $R_1$-containing molecular chain is a fluoroalkyl group or a fluoroalkenyl group, the compound of the formula (23) or (24) can also be produced by using the compound of the formula (21) or (22) as the starting material in place of 1-octadecene.

$CH_2=CHCH_2C_{10}F_{21}$ (21)
$CH_2=CH(CH_2)_9C_6F_{11}$ (22)

(23)

(24)

Furthermore, in this embodiment, the production process of the compound of the formula (I) wherein p is 9 and t is 0 was explained. In case that p and t each is the other numeral, the compound of the formula (27) or (28) can also be produced by using a monohalo-substituted fluoroalkyl carboxylate ester of the formula (25) or (26) as the starting material in place of ethyl α-bromofluoroalkylcarboxylate of the formula (18).

$C_4F_9CH_2CHI(CH_2)_8COOC_2H_5$ (25)
$C_8F_{17}CH_2CHICH_2COOC_2H_5$ (26)

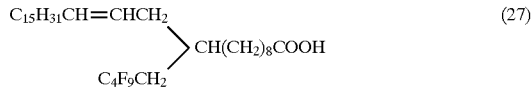
(27)

(28)

EXAMPLE 4

Hereinafter, the fourth embodiment of the present invention will be explained in detail.

The compound of this embodiment is represented by the formula (29), and the starting material is the fluoroalkylcarboxylic acid of the formula (17) obtained in Example 3.

(29)

Comparing the compound of the formula (29) with that of the general formula of the formula (I), it is one wherein the $R_1$-containing molecular chain ($R_1$—$R_2$—) is an aliphatic hydrocarbon group having 18 carbon atoms, Rf is a fluoroalkyl group having 8 carbon atoms, p is 9, q is 0, r is 0 and t is 0.

Next, the production process of the compound of the formula (29) will be explained.

Palladium black (0.5 g) was charged in a 1 liter flask equipped with a stirring blade, and 300 ml of tetrahydrofuran (THF) wherein the fluoroalkylcarboxylic acid (42.8 g, 0.05 mol) of the formula (17) was dissolved was continuously added while passing the dried high-purity nitrogen. Then, the mixture was continuously stirred at room temperature for 3 hours while bubbling a high-purity hydrogen gas through a bubbler provided under a liquid level of THF to complete the reaction. After the completion of the reaction, the reaction solution was filtered under a reduced pressure and the catalyst was removed. Then, THF was distilled off and the reaction product was recrystallized from an ethanol solution at 0° C. to give 40 g of a white solid having a melting point of 41° C. This white solid was subjected to $^{13}C$—NMR, IR, GPC and FD-MS. As a result, it has been found that the white solid is a fluoroalkylcarboxylic acid of the formula (29), which contains no starting material and by-product.

$^{13}C$—NMR: Signal of double bond at 125.5 and 128.0 ppm was disappeared.

Figure 4:
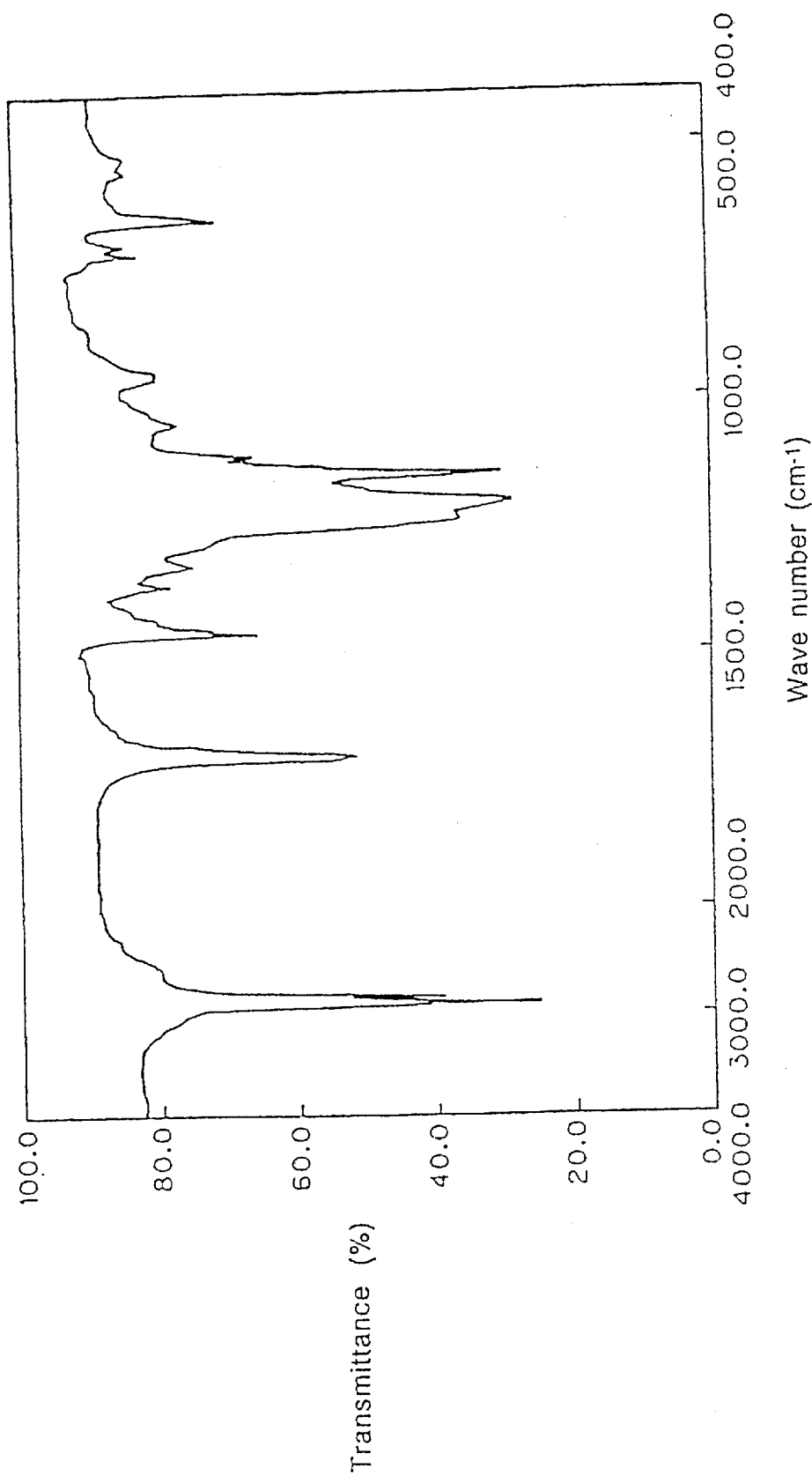
FIG. 4 shows an IR spectrum chart of the product obtained in Example 4.

IR: Absorption peak at 1700 cm$^{-1}$ of carboxylic acid was shown (FIG. 4).

GPC: No starting material and by-product were detected.

FD-MS: Main peak was shown at m/e 857.

Further, in this embodiment, the production process of the compound of the formula (I) wherein the $R_1$-containing molecular chain is an aliphatic hydrocarbon group having 18 carbon atoms was explained. In case of the aliphatic hydrocarbon group having different chain length, the compound can also be produced according to the same manner as described above. In addition, in case that the $R_1$-containing molecular chain is a fluoroalkyl group or a fluoroalkenyl group, the compound of the formula (30) or (31) can also be produced by using that of the formula (23) or (24) as the starting material in place of that of the formula (17).

  (30)

  (31)

Furthermore, in this embodiment, the production process of the compound of the formula (I) wherein p is 9 and t is 0 was explained. In case that p and t each is the other numeral, the compound of the formula (32) or (33) can also be produced by using the compound of the formula (27) or (28) as the starting material in place of that of the formula (17).

  (32)

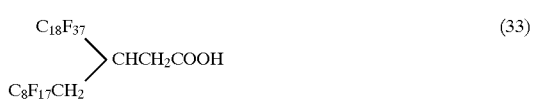  (33)

EXAMPLE 5

Hereinafter, the fifth embodiment of the present invention will be explained in detail.

The compound of this embodiment is represented by the same formula (29) as that of Example 4, but the production process is different from that of Example 4. The starting material is the fluoroalkylcarboxylate intermediate of the formula (20) obtained in Example 3.

Next, the production process of the compound of the formula (29) using the compound of the formula (20) as the starting material will be explained.

$NaBH_4$ (metal hydride) (3.8 g, 0.10 mol) and anhydrous ethanol (300 ml) were charged in a 1 liter flask equipped with a stirring blade and, after heating to a reflux temperature, 150 ml of a hexane solution wherein the fluoroalkylcarboxylate ester (46.8 g, 0.05 mol) of the formula (20) was dissolved was added dropwise over about 3 hours while stirring. Then, the mixture was continuously stirred under reflux for 4 hours to complete the reaction. After the completion of the reaction, 100 ml of the distilled water was carefully added dropwise to the reaction solution under an ice temperature to deactivate the excess metal hydride. Then, 100 ml of 3N hydrochloric acid was added to this solution and, after stirring for 5 minutes, the aqueous layer was removed. After 300 ml of ethyl acetate was added, the solution was repeatedly washed with the distilled water until the pH became 7, and dried over anhydrous sodium sulfate. Then, ethyl acetate was distilled off and the reaction product was recrystallized from an acetone solution at $-10°$ C. to give 39 g of a fluoroalkylcarboxylate ester of the formula (34) as the intermediate.

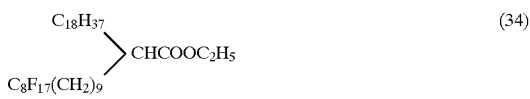  (34)

This fluoroalkylcarboxylate ester (39 g, 0.046 mol) was charged in a 1 liter flask equipped with a stirring blade and 300 ml of a 90% isopropyl alcohol solution (containing 10 volume % of distilled water) wherein 10 g of sodium hydroxide was dissolved was added, and the mixture was refluxed for 3 hours. After cooling the solution, 300 ml of 4N hydrochloric acid was slowly added with stirring and the solution was stirred at 70° C. for 2 hours. Then, the reaction product was filtered under a reduced pressure and dissolved in 300 ml of ethyl acetate. The solution was repeatedly washed with the distilled water until the pH became 7, and dried over anhydrous sodium sulfate. Then, ethyl acetate was distilled off and the reaction product was recrystallized from an ethanol solution at 0° C. to give 35 g of a white solid having a melting point of 41° C. This white solid was subjected to IR, GPC and FD-MS. As a result, it has been found that the white solid is a fluoroalkylcarboxylic acid of the formula (29), which contains no starting material, intermediate and by-product.

IR: Absorption peak at $1700$ $cm^{-1}$ of carboxylic acid was shown.

GPC: No starting material, intermediate and by-product were detected.

FD-MS: Main peak was shown at m/e 857.

EXAMPLE 6

Next, the application of the water repellent of the present invention to a metal substrate will be explained.

As the substrate, a smooth aluminum material having a maximum surface roughness ($R_{max}$) of 3 to 4 $\mu m$ was used. The water repellent of the present invention was applied on the substrate so that the coating weight was 1 $\mu g$ per 1 $cm^2$, and the water repellency and oil repellency of the resulting sample were examined. The water repellency was examined by transferring 1 $\mu l$ of the distilled water from a tip of an injection needle to the surface of the horizontally positioned sample and immediately measuring a contact angle between water and the sample. Regarding the test results, the water repellency was classified into four classes according to the following criteria.

Class A: 120° or more

Class B: 110° to 119°

Class C: 100° to 109°

Class D: 100° or less

The oil repellency was examined by using the method according to a standard testing method of AATCC 118-1992. Regarding the test results, the oil repellency was classified into classes of 0.0 (minimum) to 8.0 (maximum). These test results are shown in Table 1.

TABLE 1

| Water repellent | | Water repellency (class) | Oil repellency (class) |
|---|---|---|---|
| Example | | | |
| Formula (1) | $C_8F_{17}(CH_2)_2S$—$CH(CH_2)_8COOH$ / $C_8F_{17}CH_2$ | B | 4.0 |
| Formula (7) | $C_{10}H_{21}S$—$CH(CH_2)_8COOH$ / $C_8F_{17}CH_2$ | B | 2.0 |
| Formula (10) | $C_8F_{17}(CH_2)_2S$—$CHCH_2COOH$ / $C_8F_{17}CH_2$ | B | 5.0 |
| Formula (11) | $C_{16}H_{33}$—$CHCOOH$ / $C_8F_{17}(CH_2)_2S$ | B | 1.0 |
| Formula (15) | $C_6F_{11}(CH_2)_9$—$CHCOOH$ / $C_8F_{17}(CH_2)_2S$ | B | 3.5 |
| Formula (16) | $C_{10}H_{21}S$—$CHCOOH$ / $C_8F_{17}(CH_2)_9$ | B | 2.5 |
| Formula (17) | $C_{15}H_{31}CH{=}CHCH_2$—$CHCOOH$ / $C_8F_{17}(CH_2)_9$ | A | 1.5 |
| Formula (23) | $C_{10}F_{21}CH{=}CHCH_2$—$CHCOOH$ / $C_8F_{17}(CH_2)_9$ | A | 4.0 |
| Formula (27) | $C_{15}H_{31}CH{=}CHCH_2$—$CH(CH_2)_8COOH$ / $C_4F_9CH_2$ | A | 0.5 |
| Formula (28) | $C_{15}H_{31}CH{=}CHCH_2$—$CHCH_2COOH$ / $C_8F_{17}CH_2$ | A | 1.0 |
| Formula (29) | $C_{18}H_{37}$—$CHCOOH$ / $C_8F_{17}(CH_2)_9$ | A | 1.5 |
| Formula (31) | $C_6F_{11}(CH_2)_{11}$—$CHCOOH$ / $C_8F_{17}(CH_2)_9$ | A | 3.0 |
| Formula (32) | $C_{18}H_{37}$—$CH(CH_2)_8COOH$ / $C_4F_9CH_2$ | A | 0.5 |
| Formula (33) | $C_{18}H_{37}$—$CHCH_2COOH$ / $C_8F_{17}CH_2$ | A | 1.0 |
| Comparative Example | | | |
| Compound example of formula (i) | $[C_8F_{17}(CH_2)_2S]_2C(CH_3)COOH$ | C | 5.0 |
| Non-treated | | D | 0.0 |

As is apparent from Table 1, all water repellents of the present invention can impart a high water repellency to the smooth aluminum material and can widely change the oil repellency within a wide range of 0.5 (low) to 5.0 (high).

EXAMPLE 7

Next, the application of the water repellent of the present invention to a fiber substrate will be explained.

As the substrate, a 100% cotton fabric was used. The water repellent of the present invention was applied to this substrate so that the coating weight was 0.1% of the fabric weight, and the water repellency and oil repellency of the resulting sample were examined. The water repellency was examined by the method according to a spray testing method of JIS L1092. Regarding the test results, the water repellency was classified into points of 0 (minimum) to 100 (maximum). The oil repellency was examined by using the method according to a standard testing method of AATCC 118-1992. Regarding the test results, the oil repellency was classified into classes of 0.0 (minimum) to 8.0 (maximum). These test results are shown in Table 2.

TABLE 2

| Water repellent | | Water repellency (point) | Oil repellency (class) |
|---|---|---|---|
| Example | | | |
| Formula (1) | $C_8F_{17}(CH_2)_2S$—$CH(CH_2)_8COOH$ / $C_8F_{17}CH_2$ | 100 | 5.0 |
| Derivative from formula (7) | $C_{10}H_{21}S$—$CH(CH_2)_8COCl$ / $C_8F_{17}CH_2$ | 100 | 2.0 |
| Derivative from formula (10) | $C_8F_{17}(CH_2)_2S$—$CH(CH_2)_2OH$ / $C_8F_{17}CH_2$ | 100 | 6.0 |

TABLE 2-continued

| Water repellent | | Water repellency (point) | Oil repellency (class) |
|---|---|---|---|
| Derivative from formula (11) | $C_{16}H_{33}$\CHCONH$_2$ / $C_8F_{17}(CH_2)_2S$ | 100 | 1.5 |
| Derivative from formula (15) | $C_6F_{11}(CH_2)_9$\CHCH$_2$NH$_2$ / $C_8F_{17}(CH_2)_2S$ | 100 | 4.0 |
| Derivative from formula (16) | $C_{10}H_{21}S$\CHCOCl / $C_8F_{17}(CH_2)_9$ | 100 | 2.5 |
| Formula (17) | $C_{15}H_{31}CH\!=\!CHCH_2$\CHCOOH / $C_8F_{17}(CH_2)_9$ | 100 | 2.0 |
| Derivative from formula (23) | $C_{10}F_{21}CH\!=\!CHCH_2$\CHCOCl / $C_8F_{17}(CH_2)_9$ | 100 | 4.5 |
| Derivative from formula (27) | $C_{15}H_{31}CH\!=\!CHCH_2$\CH(CH$_2$)$_9$OH / $C_4F_9CH_2$ | 100 | 1.0 |
| Derivative from formula (28) | $C_{15}H_{31}CH\!=\!CHCH_2$\CHCH$_2$CONH$_2$ / $C_8F_{17}CH_2$ | 100 | 1.5 |
| Derivative from formula (29) | $C_{18}H_{37}$\CHCH$_2$NH$_2$ / $C_8F_{17}(CH_2)_9$ | 100 | 2.0 |
| Formula (31) | $C_6F_{11}(CH_2)_{11}$\CHCOOH / $C_8F_{17}(CH_2)_9$ | 100 | 4.0 |
| Derivative from formula (32) | $C_{18}H_{37}$\CH(CH$_2$)$_8$COCl / $C_4F_9CH_2$ | 100 | 1.0 |
| Derivative from formula (33) | $C_{18}H_{37}$\CH(CH$_2$)$_2$OH / $C_8F_{17}CH_2$ | 100 | 1.5 |
| Comparative Example | | | |
| Compound example of formula (i) | $[C_8F_{17}(CH_2)_2S]_2C(CH_3)COOH$ | 90 | 6.0 |
| Non-treated | | 0 | 0.0 |

As is apparent from Table 2, all water repellents of the present invention can impart a high water repellency to the cotton fabric and can widely change the oil repellency within a wide range of 1.0 (low) to 6.0 (high).

As is apparent from the above explanation, the fluoroalkylcarboxylic acid and its derivative of the present invention, which have molecular chains and a polar group in the same molecule, wherein one molecular chain is a fluoroalkyl group or a fluoroalkenyl group and another molecular chain is an aliphatic hydrocarbon group, a fluoroalkyl group or a fluoroalkenyl group, and wherein only one molecular chain contains a sulfur atom or contains no sulfur atom and the number of carbon atoms of an alkylene group which bonds with these groups can be widely changed. Therefore, they are useful for applications as the water repellent capable of widely changing the oil repellency or lipophilic property, and raw materials and intermediates in the fluorochemical industry.

What is claimed is:

1. A fluoroalkylcarboxylic acid derivative which is a fluoroalkyl compound of the general formula:

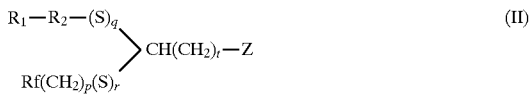

(II)

wherein $R_1$ is a fluoroalkyl, fluoroalkenyl or aliphatic hydrocarbon group having 1 to 20 carbon atoms; $R_2$ is an alkylene or alkenylene group having 1 to 11 carbon atoms; Rf is a fluoroalkyl or fluoroalkenyl group having 1 to 20 carbon atoms; Z is $CH_2OH$, $COCl$, $CONH_2$ or $CH_2NH_2$; p is an integer of 1 to 11; q+r is 0 or 1; and t is 0 or an integer of 1 to 8; provided that p is an integer of 3 to 11 when $R_1$ is an aliphatic hydrocarbon group, $R_2$ is an alkylene group, q+r is 0 and t is 0.

2. A water repellent composition comprising the fluoroalkylcarboxylic acid derivative according to claim 1.

3. A water repellant composition comprising a fluorocarboxylic acid of the general formula:

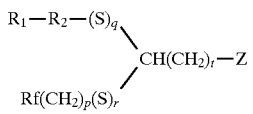

wherein $R_1$ is a fluoroalkyl, fluoroalkenyl or aliphatic hydrocarbon group having 1 to 20 carbon atoms; $R_2$ is an alkylene or alkenylene group having 1 to 11 carbon atoms; Rf is a fluoroalkyl or fluroalkenyl group having 1 to 20 carbon atoms; Z is $CH_2OH$, $COCl$, $CONH_2$, $CH_2NH_2$; p is an integer of 1 to 11; q+r is 0 or 1; and t is 0 or an integer of 1 to 8; provided that p is an integer or 3 to 11 when $R_1$ is an aliphatic hydrocarbon group, $R_2$ is an alkylene group, q+r is 0 and t is 0.

4. A water repellent composition comprising at least one of the fluoroalkylcarboxylic acid of the formula

(I)

wherein $R_1$ is a fluoroalkyl, fluoroalkenyl or aliphatic hydrocarbon group having 1 to 20 carbon atoms; $R_2$ is an alkylene or alkenylene group having 1 to 11 carbon atoms; Rf is a fluoroalkyl or fluoroalkenyl group having 1 to 20 carbon atoms; p is an integer of 1 to 11; q+r is 0 or 1; and t is 0 or an integer of 1 to 8; provided that p is an integer of 3 to 11 when $R_1$ is an aliphatic hydrocarbon group, $R_2$ is an alkylene group, q+r is 0 and t is 0;

and the fluoroalkylcarboxylic acid derivative of the formula

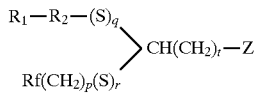 (II)

wherein $R_1$ is a fluoroalkyl, fluoroalkenyl or aliphatic hydrocarbon group having 1 to 20 carbon atoms; $R_2$ is an alkylene or alkenylene group having 1 to 11 carbon atoms; Rf is a fluoroalkyl or fluoroalkenyl group having 1 to 20 carbon atoms; Z is $CH_2OH$, $COCl$, $CONH_2$ or $CH_2NH_2$; p is an integer of 1 to 11; q+r is 0 or 1; and t is 0 or an integer of 1 to 8; provided that p is an integer of 3 to 11 when $R_1$ is an aliphatic hydrocarbon group, $R_2$ is an alkylene group, q+r is 0 and t is 0.

* * * * *